(12) United States Patent
Aketa et al.

(10) Patent No.: US 7,008,697 B2
(45) Date of Patent: Mar. 7, 2006

(54) AIR BAG SEALER SILICONE RUBBER COMPOSITION

(75) Inventors: Takashi Aketa, Gunma-ken (JP); Hiroyasu Hara, Gunma-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 96 days.

(21) Appl. No.: 10/705,828

(22) Filed: Nov. 13, 2003

(65) Prior Publication Data

US 2004/0096673 A1 May 20, 2004

(30) Foreign Application Priority Data

Nov. 14, 2002 (JP) .............................. 2002-330626

(51) Int. Cl.
*B32B 9/04* (2006.01)

(52) U.S. Cl. .................... 428/447; 528/15; 528/31; 528/32; 525/478; 525/479

(58) Field of Classification Search ................. 528/31, 528/32; 525/477, 479
See application file for complete search history.

(56) References Cited

U.S. PATENT DOCUMENTS

| | | |
|---|---|---|
| 3,159,601 A | 12/1964 | Ashby |
| 3,159,662 A | 12/1964 | Ashby |
| 3,220,972 A | 11/1965 | Lamoreaux |
| 3,755,452 A | 8/1973 | Sinn et al. |
| 4,257,936 A | 3/1981 | Matsumoto et al. |
| 5,106,933 A * | 4/1992 | Kobayashi et al. ........... 528/15 |
| 5,399,402 A | 3/1995 | Inoue et al. |
| 5,424,357 A * | 6/1995 | Larson ...................... 524/765 |
| 5,789,084 A | 8/1998 | Nakamura et al. |
| 5,877,256 A | 3/1999 | Nakamura et al. |
| 6,387,520 B1 | 5/2002 | Fujiki et al. |
| 6,425,600 B1 | 7/2002 | Fujiki et al. |
| 2003/0211340 A1 * | 11/2003 | Ikeno et al. ................. 428/447 |

FOREIGN PATENT DOCUMENTS

| | | |
|---|---|---|
| EP | 0 663 468 A1 | 7/1995 |
| JP | 58-26376 B2 | 6/1983 |
| JP | 7-3164 A * | 1/1995 |
| JP | 2001-1854 A | 1/2001 |

OTHER PUBLICATIONS

Abstract for JP 7-3164.*

* cited by examiner

*Primary Examiner*—Marc S Zimmer
(74) *Attorney, Agent, or Firm*—Birch, Stewart, Kolasch & Birch, LLP

(57) ABSTRACT

When silicone rubber-impregnated and/or coated fabric pieces are mated, with their treated surfaces inside, and joined along a periphery to form a bag, a silicone rubber composition having a tris(trialkoxysilylalkyl) isocyanurate blended as an adhesion promoter is used as a sealer where the peripheral portions of the fabric pieces are joined together whereby an improved bond is established therebetween.

4 Claims, No Drawings

AIR BAG SEALER SILICONE RUBBER COMPOSITION

This Nonprovisional application claims priority under 35 U.S.C. § 119(a) on Patent Application No(s). 2002-330626 filed in JAPAN on Nov. 14, 2002, the entire contents of which are hereby incorporated by reference.

TECHNICAL FIELD

This invention relates to a silicone rubber composition for use as an air bag sealer.

BACKGROUND OF THE INVENTION

One typical process for preparing an air bag involves the steps of furnishing a pair of base fabric pieces impregnated and/or coated with silicone rubber, laying the pieces one on the other, with the impregnated or coated surfaces of the pieces inside, and bonding or stitching peripheral portions of the pieces together to form a bag. It has been practiced to apply an adhesive silicone rubber composition as a sealer to the peripheral portions of the base fabric pieces prior to bonding or stitching.

For imparting adhesiveness to silicone rubber compositions, it is customary in the silicone art to add γ-glycidoxypropyltrimethoxysilane, phenyltrimethoxysilane or an adhesion promoter of the following structure as described in JP-B 58-26376 corresponding to U.S. Pat. No. 4,257,936.

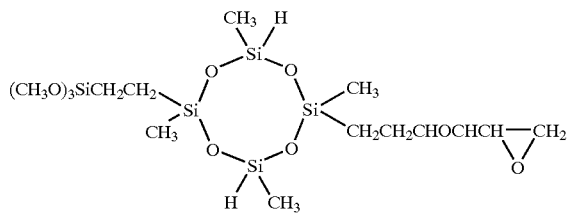

The resulting (uncured) silicone rubber compositions develop adhesiveness to metals and plastics, but are still very difficult to bond to once cured silicone rubber.

SUMMARY OF THE INVENTION

An object of the present invention is to provide, in connection with the aforementioned air bag preparation process, a silicone rubber composition which is applicable as a sealer to the peripheral portions of the silicone rubber-impregnated or coated base fabric pieces prior to joining and develops good adherence to the once cured silicone rubber.

In connection with a process of preparing an air bag by laying a pair of base fabric pieces impregnated and/or coated with silicone rubber one on the other, with the impregnated or coated surfaces of the pieces inside, and bonding or stitching peripheral portions of the pieces together to form a bag, the present invention provides an adhesive silicone rubber composition having a compound of the general formula (1) added as adhesion promoter. The silicone rubber composition is suited for use as a sealer to be applied to the peripheral portions of the base fabric pieces prior to bonding or stitching and develops good adherence to the base fabric pieces.

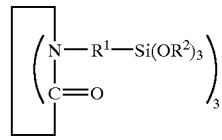

Herein $R^1$ is an alkylene radical having 1 to 6 carbon atoms and $R^2$ is a methyl, ethyl or propyl radical.

Preferably the silicone rubber composition comprises:
(A) 100 parts by weight of an organopolysiloxane containing on average at least two silicon atom-bonded alkenyl radicals in a molecule,
(B) an organohydrogenpolysiloxane containing at least two silicon atom-bonded hydrogen atoms in a molecule, in an amount to give 0.5 to 5.0 silicon atom-bonded hydrogen atoms per alkenyl radical in the organopolysiloxane (A),
(C) a catalytic amount of a platinum group metal catalyst,
(D) 0.1 to 10 parts by weight of the compound of formula (1), and optionally,
(E) 0.01 to 5 parts by weight of a titanic acid ester.

DETAILED DESCRIPTION OF THE INVENTION

The air bag sealer silicone rubber composition of the present invention is a silicone rubber composition characterized by the inclusion of a compound of formula (1), and preferably a silicone rubber composition of the addition reaction curing type comprising the above-described components (A) to (C), and a compound of formula (1) as component (D). These components are described in detail.

(A) Alkenyl-Containing Organopolysiloxane

The alkenyl-containing organopolysiloxane used herein should contain at least two alkenyl radicals in a molecule. Most often, it is a linear one whose backbone consists essentially of recurring diorganosiloxane units and which is blocked with a triorganosiloxy radical at each end of its molecular chain. It may contain a branched structure in part in its molecular structure or even be cyclic. From the standpoint of mechanical strength and other physical properties of the cured product, a linear diorganopolysiloxane is preferred. The alkenyl radicals may be attached only at the ends of the molecular chain or at the ends and intermediates of the molecular chain. Typically, the alkenyl-containing organopolysiloxane are represented by the general formula (2).

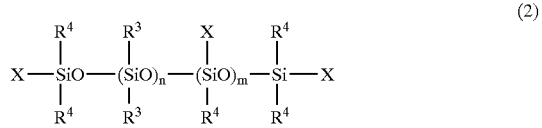

Herein X is an alkenyl radical, $R^3$ is independently a substituted or unsubstituted monovalent hydrocarbon radical free of aliphatic unsaturation, $R^4$ is X or $R^3$, n and m each are 0 or an integer of at least 1.

Examples of suitable substituted or unsubstituted monovalent hydrocarbon radicals free of aliphatic unsaturation represented by $R^3$ include alkyl radicals such as methyl, ethyl, propyl, isopropyl, butyl, isobutyl, tert-butyl, pentyl, neopentyl, hexyl, heptyl, octyl, nonyl, decyl and dodecyl; cycloalkyl radicals such as cyclopentyl, cyclohexyl and cycloheptyl; aryl radicals such as phenyl, tolyl, xylyl, naphthyl and biphenylyl; aralkyl radicals such as benzyl, phenylethyl, phenylpropyl and methylbenzyl; and substituted radicals of the foregoing in which some or all of the carbon atom-bonded hydrogen atoms are substituted with halogen atoms (e.g., fluoro, chloro, bromo), cyano radicals or the like, such as chloromethyl, 2-bromoethyl, 3-chloropropyl, 3,3,3-trifluoropropyl, chlorophenyl, fluorophenyl, cyanoethyl and 3,3,4,4,5,5,6,6,6-nonafluorohexyl. Those radicals having 1 to 10 carbon atoms, especially 1 to 6 carbon atoms are typical. Of these, preferred are substituted or unsubstituted alkyl radicals having 1 to 3 carbon atoms such as methyl, ethyl, propyl, chloromethyl, bromoethyl, 3,3,3-trifluoropropyl and cyanoethyl and substituted or unsubstituted phenyl radicals such as phenyl, chlorophenyl and fluorophenyl.

Examples of suitable alkenyl radicals represented by X include those having about 2 to about 8 carbon atoms such as vinyl, allyl, propenyl, isopropenyl, butenyl, hexenyl and cyclohexenyl, with lower alkenyl radicals such as vinyl and allyl being preferred.

In formula (2), n is an integer of 0, 1 or greater, m is an integer of 0, 1 or greater. Preferably n and m are integers satisfying $10 \leq n+m \leq 10,000$, and more preferably $50 \leq n+m \leq 2,000$ and $0 \leq m/(n+m) \leq 0.2$.

These alkenyl-containing organopolysiloxanes should preferably have a viscosity of 10 to 1,000,000 cSt at 25° C., more preferably 100 to 500,000 cSt at 25° C.

(B) Organohydrogenpolysiloxane

The organohydrogenpolysiloxane contains at least two, preferably at least three hydrogen atoms each attached to a silicon atom (i.e., SiH radicals) in a molecule. The organohydrogenpolysiloxane may have a linear, branched or cyclic structure or be a resinous one having three-dimensional network structure.

Most often, the organohydrogenpolysiloxane (B) is represented by the following average compositional formula (3).

$$H_a R^5_b SiO_{(4-a-b)/2} \quad (3)$$

In formula (3), $R^5$ is independently a substituted or unsubstituted monovalent hydrocarbon radical free of aliphatic unsaturation, "a" and "b" are numbers satisfying $0<a<2$, $0.8 \leq b \leq 2$ and $0.8<a+b \leq 3$, and preferably $0.05 \leq a \leq 1$, $1.5 \leq b \leq 2$ and $1.8 \leq a+b \leq 2.7$.

Examples of suitable substituted or unsubstituted monovalent hydrocarbon radicals free of aliphatic unsaturation represented by $R^5$ are as exemplified for $R^3$ in formula (2). Monovalent hydrocarbon radicals having 1 to 10 carbon atoms, especially 1 to 7 carbon atoms are typical. Of these, lower alkyl radicals having 1 to 3 carbon atoms such as methyl and 3,3,3-trifluoropropyl are preferred as well as phenyl.

Examples of the organohydrogenpolysiloxane include siloxane oligomers such as 1,1,3,3-tetramethyldisiloxane, 1,3,5,7-tetramethyltetracyclosiloxane, and 1,3,5,7,8-pentamethylpentacyclosiloxane; both end trimethylsiloxy-blocked methylhydrogenpolysiloxane, both end trimethylsiloxy-blocked dimethylsiloxane-methylhydrogensiloxane copolymers, both end silanol-blocked methylhydrogenpolysiloxane, both end silanol-blocked dimethylsiloxane-methylhydrogensiloxane copolymers, both end dimethylhydrogensiloxy-blocked dimethylpolysiloxane, both end dimethylhydrogensiloxy-blocked methylhydrogenpolysiloxane, both end dimethylhydrogensiloxy-blocked dimethylsiloxane-methylhydrogensiloxane copolymers; and silicone resins comprising $R_2(H)SiO_{1/2}$ units and $SiO_{4/2}$ units and optionally, $R_3SiO_{1/2}$ units, $R_2SiO_{2/2}$ units, $R(H)SiO_{2/2}$ units, $(H)SiO_{3/2}$ units or $RSiO_{3/2}$ units wherein R is a substituted or unsubstituted monovalent hydrocarbon radical as exemplified above for $R^3$. Also included are those represented by the following formulae:

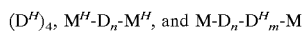

$(D^H)_4$, $M^H-D_n-M^H$, and $M-D_n-D^H_m-M$ wherein M is a $R_3SiO_{1/2}$ unit, D is a $R_2SiO_{2/2}$ unit, $M^H$ is a $R_2(H)SiO_{1/2}$ unit, $D^H$ is a $R(H)SiO_{2/2}$ unit, and m and n are as defined in formula (2).

The organohydrogenpolysiloxane used herein can be prepared by well-known methods, for example, by co-hydrolyzing at least one chlorosilane selected from the general formulae: $R^5SiHCl_2$ and $R^5_2SiHCl$ wherein $R^5$ is as defined above, or by co-hydrolyzing a mixture of the foregoing chlorosilane and at least one chlorosilane selected from the general formulae: $R^5_3SiCl$ and $R^5_2SiCl_2$ wherein $R^5$ is as defined above. If desired, the polysiloxane resulting from such cohydrolysis is further subjected to equilibration reaction, resulting in an organohydrogenpolysiloxane which is also useful.

Component (B) is preferably used in such amounts that 0.5 to 5.0 moles, more preferably 0.8 to 2.5 moles of silicon atom-bonded hydrogen atoms (i.e., SiH radicals) in the organohydrogenpolysiloxane (B) are present per mole of alkenyl radicals in the alkenyl-containing organopolysiloxane (A).

(C) Platinum Group Metal Catalyst

The platinum group metal catalyst used herein is a catalyst for promoting the addition reaction between alkenyl radicals in component (A) and silicon atom-bonded hydrogen atoms in component (B). Well-known catalysts used in hydrosilylation reaction are useful. Exemplary catalysts are platinum, palladium and rhodium base catalysts including elemental platinum group metals such as platinum (inclusive of platinum black), rhodium and palladium; platinum chloride, chloroplatinic acid and chloroplatinic acid salts such as $H_2PtCl_4 \cdot nH_2O$, $H_2PtCl_6 \cdot nH_2O$, $NaHPtCl_6 \cdot nH_2O$, $KHPtCl_6 \cdot nH_2O$, $Na_2PtCl_6 \cdot nH_2O$, $K_2PtCl_4 \cdot nH_2O$, $PtCl_4 \cdot nH_2O$, $PtCl_2$ and $Na_2HPtCl_4 \cdot nH_2O$ wherein n is an integer of 0 to 6, preferably 0 or 6; alcohol-modified chloroplatinic acid (see U.S. Pat. No. 3,220,972); complexes of chloroplatinic acid with olefins (see U.S. Pat. Nos. 3,159,601, 3,159,662 and 3,775,452); platinum group metals such as platinum black and palladium on carriers such as alumina, silica and carbon; rhodium-olefin complexes; chlorotris(triphenylphosphine)rhodium (known as Wilkinson catalyst); and complexes of platinum chloride, chloroplatinic acid or chloroplatinic acid salts with vinyl-containing siloxanes, especially vinyl-containing cyclic siloxanes.

The catalyst (C) is used in a catalytic amount, typically about 0.1 to 500 parts, preferably about 0.5 to 200 parts by weight of platinum group metal per million parts by weight of components (A) and (B) combined.

(D) Adhesion Promoter

The air bag sealer silicone rubber composition of the present invention contains a compound of the general formula (1) as adhesion promoter.

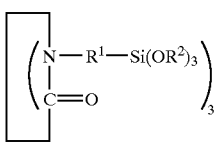

Herein $R^1$ is an alkylene radical having 1 to 6 carbon atoms and $R^2$ is methyl, ethyl or propyl.

Illustrative examples of the compound of formula (1) are given below.

a compound of the structure shown below, named tris[3-(trimethoxysilyl)propyl] isocyanurate according to IUPAC nomenclature.

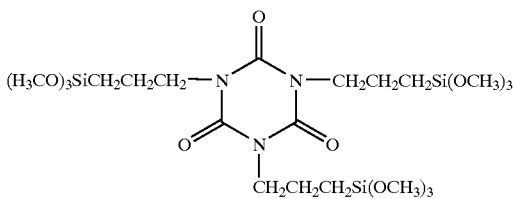

a compound of the structure shown below, named tris[3-(triethoxysilyl)propyl] isocyanurate according to IUPAC nomenclature.

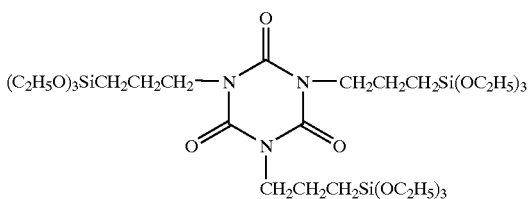

a compound of the structure shown below, named tris[3-(tripropoxysilyl)propyl] isocyanurate according to IUPAC nomenclature.

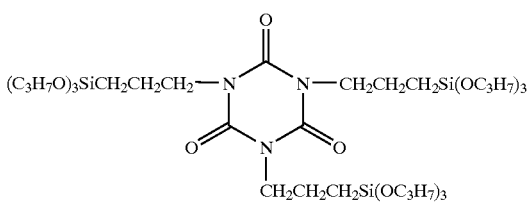

An appropriate amount of component (D), compound of formula (1) blended is 0.1 to 10 parts by weight, more preferably 0.5 to 3 parts by weight per 100 parts by weight of the organopolysiloxane (A). Too less amounts of component (D) may fail to develop a sufficient degree of adhesion whereas excessive amounts may detract from the fluidity of the composition.

(E) Titanic Acid Ester

If desired, a titanic acid ester is blended in the silicone rubber composition of the invention. The titanic acid ester cooperates with component (D) to further enhance the adhesiveness-imparting effect of component (D). Examples of the titanic acid ester include tetraalkoxytitanium compounds such as tetraisopropoxytitanium and tetra-n-butoxytitanium.

An appropriate amount of component (E) blended is up to 5 parts by weight (0 to 5 parts by weight), preferably 0.01 to 5 parts by weight, more preferably 0.1 to 1.0 part by weight per 100 parts by weight of the organopolysiloxane (A). Too less amounts of component (E) fail to achieve the addition effect whereas excessive amounts of the titanic acid ester generate more alcohol upon hydrolysis, with a possibility to disrupt the crosslinker.

Other Components

In addition to the above-described components (A) to (E), there may be added to the inventive composition reinforcing inorganic fillers such as fumed silica and fumed titanium dioxide; reinforcing silicone resins; and non-reinforcing inorganic fillers such as calcium silicate, titanium dioxide, ferric oxide, and carbon black. These inorganic fillers are generally used in amounts of 0 to 200 parts by weight per 100 parts by weight of components (A) to (D) combined. It is also acceptable to add organic titanium compounds such as titanium chelates. The organic titanium compounds are generally used in amounts of 0 to 10 parts by weight, preferably 0.1 to 5 parts by weight per 100 parts by weight of components (A) to (D) combined. Besides, organosilicon compounds such as silanes and siloxanes having at least one functional radical selected from epoxy, alkoxysilyl, carbonyl and phenyl radicals may be added to the composition as a tackifier.

Additionally, calcium carbonate may be blended in the inventive silicone rubber composition because the cured silicone rubber is improved in elongation at break and adherence. Calcium carbonate powder has a certain basicity. The calcium carbonate powder used herein may be selected from well-known ones such as heavy calcium carbonate and colloidal calcium carbonate. These calcium carbonate powders have not been surface treated, but may be surface treated with resin acids or fatty acids. From the standpoints of fluidity and reinforcement, calcium carbonate powder having an average particle size of 0.05 to 50 μm, especially 0.5 to 50 μm is preferred. While the calcium carbonate powder generally retains some moisture, it is desired to remove moisture. Moisture removal is carried out, for example, by mixing a dimethylpolysiloxane with calcium carbonate powder and heat treating the mixture. The heating temperature is usually 50° C. or higher, preferably 80 to 200° C., and a reduced pressure may be employed for promoting the heat treatment. By this heat treatment, the calcium carbonate powder which has not been surface treated is substantially treated with the dimethylpolysiloxane whereby the moisture is released. When the addition reaction curing type silicone rubber composition is loaded with such dry calcium carbonate powder, the composition can be stabilized without chemically altering the organohydrogenpolysiloxane (B).

The calcium carbonate powder is preferably-blended in amounts of 0 to about 200 parts by weight, more preferably about 5 to 50 parts by weight per 100 parts by weight of components (A) to (D) combined.

Like conventional curable silicone rubber compositions, the inventive composition may be formulated as a two part composition wherein two parts are kept separate and on use, mixed together for curing. Independent of whether the inventive composition is one part type or two part type, an epoxy radical-containing polysiloxane compound or ester siloxane compound may be additionally included in the composition, if desired, for improving the adhesion of the composition. Under the same conditions as used for well-known addition reaction curing type silicone rubber compositions, the inventive composition can be cured. For example, the inventive composition cures satisfactorily at room temperature, but can be heated for curing if desired.

The silicone rubber composition of the invention is used as a sealer for an air bag, which is typically prepared by furnishing a pair of base fabric pieces impregnated and/or coated with silicone rubber, laying the pieces one on the other, with the impregnated or coated surfaces of the pieces faced inside, and bonding or stitching peripheral portions of the pieces together to form a bag.

In sealing the air bag using the silicone rubber composition of the present invention, the inventive silicone rubber composition is applied and cured to the peripheral portions of the plain weave fabric pieces to be stitched as disclosed in JP-A 2001-1854. The resulting silicone rubber serves as a seam sealer.

EXAMPLE

Examples of the invention are given below by way of illustration and not by way of limitation. All parts are by weight.

The materials used in Examples are listed below.

(A-1) Tackifier
   phenyltrimethoxysilane (KBM103 by Shin-Etsu Chemical Co., Ltd.)

(A-2) Tackifier
   γ-glycidoxypropyltrimethoxysilane (KBM403 by Shin-Etsu Chemical Co., Ltd.)

(A-3) Tackifier
   tris(3-trimethoxysilylpropyl) isocyanurate (Aldrich Chemical Company, Inc.)

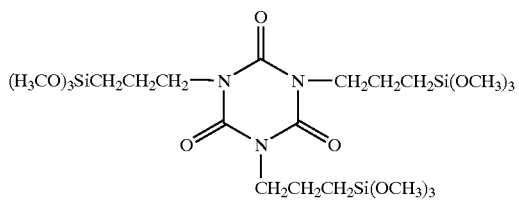

(A-4) Tackifier
   tris(3-triethoxysilylpropyl) isocyanurate (Aldrich Chemical Company, Inc.)

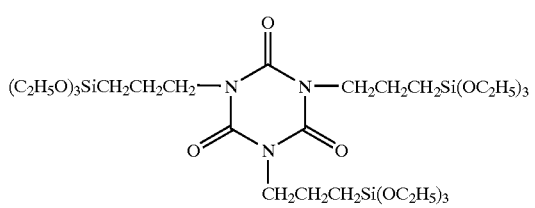

(A-5) Tackifier
   tris(3-tripropoxysilylpropyl) isocyanurate (Aldrich Chemical Company, Inc.)

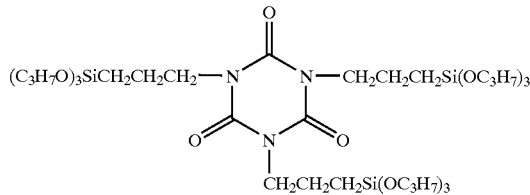

(B) Organopolysiloxane
   Vinyl-containing linear organopolysiloxane represented by the formula:

$$Vi(Me)_2Si{-}(OSiMe_2)_n{-}OSi(Me)_2Vi$$

wherein Me is methyl, Vi is vinyl, and n is such a number that the siloxane has a viscosity of 100,000 cSt at 25° C.

(C-1) Organohydrogenpolysiloxane
   $M^H{-}D_{18}{-}M^H$ (C-2) Organohydrogenpolysiloxane
   $M{-}D_{40}{-}DH_2{-}M$ $M^H$ is $(CH_3)_2HSiO_{1/2}$, D is $(CH_3)_2SiO$, M is $(CH_3)_3SiO_{1/2}$, and $D^H$ is $(CH_3)HSiO$.

(D) Platinum Group Metal Catalyst
   platinum-divinyltetramethyldisiloxane complex in toluene (Pt content 0.5 wt %)

(E) Organotitanium compound
   $Ti[OCH_2CH(C_2H_5)(CH_2)_3CH_3]_4$ (F) Reinforcing Resin
   vinyl-containing methylpolysiloxane resin composed of $Vi(Me)_2SiO_{1/2}$ units and $SiO_{4/2}$ units (G) Reinforcing Inorganic Filler
   fumed silica treated with dimethylpolysiloxane and hexamethyldisilazane (H) Cure Regulating Agent
   50% ethynyl cyclohexanol in toluene (I) Calcium Carbonate Powder
   Calex 300 by Maruo Calcium Co., Ltd. average particle size 0.04 μm surface treating agent: higher fatty acid (a mixture of lauric acid, myristic acid, palmitic acid, oleic acid and stearic acid)

Examples 1–4 & Comparative Examples 1–2

Runs were carried out using the foregoing materials. Components (B) and (I) were first mixed. The mixture was heat treated at 150° C. for 2 hours under a reduced pressure. After cooling to room temperature, the mixture was compounded with components (A), (C), (D), (E), (F), (G), and (H) under a reduced pressure, yielding an adhesive silicone rubber composition. The composition was examined by a peel test.

Peel Test and Cohesive Failure
   Two fabric pieces coated with silicone rubber were mated together, with the coated surfaces faced inside. At this point, the adhesive silicone rubber composition was applied therebetween to a thickness of 0.5 mm. The silicone rubber composition was cured, after which the fabric pieces were peeled apart using a testing machine Strograph. A peel adhesion strength (kgf/cm) was measured and a percent cohesive failure at the adhesion interface was computed.

The results are shown in Table 1.

TABLE 1

| Components | Example | | | | Comparative Example | |
|---|---|---|---|---|---|---|
| (pbw) | 1 | 2 | 3 | 4 | 1 | 2 |
| A-1 | 0 | 0 | 0 | 0 | 1 | 0 |
| A-2 | 0 | 0 | 0 | 0 | 0 | 1 |
| A-3 | 1 | 2 | 0 | 0 | 0 | 0 |
| A-4 | 0 | 0 | 1 | 0 | 0 | 0 |
| A-5 | 0 | 0 | 0 | 1 | 0 | 0 |
| B | 94 | 94 | 94 | 94 | 94 | 94 |
| C-1 | 1.9 | 1.9 | 1.9 | 1.9 | 1.9 | 1.9 |
| C-2 | 1 | 1 | 1 | 1 | 1 | 1 |
| D | 0.5 | 0.5 | 0.5 | 0.5 | 0.5 | 0.5 |
| E | 0.5 | 0.5 | 0.5 | 0.5 | 0.5 | 0.5 |
| F | 7.5 | 7.5 | 7.5 | 7.5 | 7.5 | 7.5 |
| G | 21 | 21 | 21 | 21 | 21 | 21 |
| H | 0.1 | 0.1 | 0.1 | 0.1 | 0.1 | 0.1 |
| I | 20 | 20 | 20 | 20 | 20 | 20 |
| Peel strength (kgf/cm) | 5.0 | 6.3 | 5.8 | 5.7 | 2.0 | 2.7 |
| Cohesive failure (%) | 100 | 100 | 100 | 100 | 0 | 20 |

In Examples 1 and 2, tris(3-trimethoxysilylpropyl) isocyanurate (Aldrich) was used as the tackifier in addition amounts of 1 part and 2 parts, with a satisfactory degree of adhesion achieved in either case. In Examples 3 and 4 wherein tris(3-triethoxysilylpropyl) isocyanurate and tris(3-tripropoxysilylpropyl) isocyanurate were used instead of tris(3-trimethoxysilylpropyl) isocyanurate (Aldrich), a satisfactory degree of adhesion was demonstrated.

In Comparative Examples 1 and 2, phenyltrimethoxysilane KBM103 and γ-glycidoxypropyltrimethoxysilane KBM403 (both by Shin-Etsu Chemical Co., Ltd.) were used, with no satisfactory degree of adhesion achieved.

When silicone rubber-impregnated and/or coated fabric pieces are mated, with their impregnated or coated surfaces inside, and joined along a periphery to form a bag, the adhesive silicone rubber compositions of Examples having blended as an adhesion promoter a compound of formula (1):

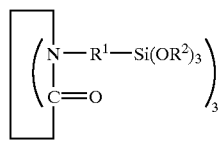

(1)

wherein $R^1$ is an alkylene radical having 1 to 6 carbon atoms and $R^2$ is methyl, ethyl or propyl, are used as a sealer where the peripheral portions of the fabric pieces are joined together whereby an improved bond is established between the peripheral portions of the fabric pieces.

In an air bag prepared by laying a pair of base fabric pieces impregnated and/or coated with silicone rubber one on the other, with the impregnated or coated surfaces of the pieces inside, and bonding or stitching peripheral portions of the pieces together to form a bag, the silicone rubber composition of the invention is used as a sealer and applied to the peripheral portions of the base fabric pieces, thereby achieving improved adhesion therebetween.

Japanese Patent Application No. 2002-330626 is incorporated herein by reference.

Reasonable modifications and variations are possible from the foregoing disclosure without departing from either the spirit or scope of the present invention as defined by the claims.

The invention claimed is:

1. A process of preparing an air bag comprising
   laying a pair of base fabric pieces impregnated and/or coated with silicone rubber one on the other, with the impregnated or coated surfaces of the pieces inside, and joining peripheral portions of the pieces together to form a bag, and
   applying a silicone rubber sealer composition to the peripheral portions of the basic fabric pieces, the composition comprising a compound having the general formula (1):

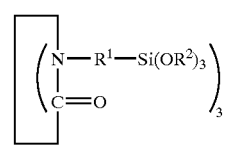

(1)

wherein $R^1$ is an alkylene radical having 1 to 6 carbon atoms and $R^2$ is a methyl, ethyl or propyl radical.

2. The process of claim 1, wherein the silicone rubber sealer composition comprises
   (A) 100 parts by weight of an organopolysiloxane containing on average at least two silicon atom-bonded alkenyl radicals in a molecule,
   (B) an organohydrogenpolysiloxane containing at least two silicon atom-bonded hydrogen atoms in a molecule, in an amount to give 0.5 to 5.0 silicon atom-bonded hydrogen atoms per alkenyl radical in the organopolysiloxane (A),
   (C) a catalytic amount of a platinum group metal catalyst, and
   (D) 0.1 to 10 parts by weight of the compound of formula (1).

3. The process of claim 2, wherein the silicone rubber sealer composition further comprises
   (E) 0.01 to 5 parts by weight of a titanic acid ester per 100 parts by weight of the organopolysiloxane (A).

4. An air bag obtained by effecting the process of claim 1, 2, or 3.

* * * * *